United States Patent
Matsumoto

(10) Patent No.: US 6,488,377 B2
(45) Date of Patent: Dec. 3, 2002

(54) OPHTHALMIC IMAGING APPARATUS

(75) Inventor: Kazuhiro Matsumoto, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 71 days.

(21) Appl. No.: 09/805,131

(22) Filed: Mar. 14, 2001

(65) Prior Publication Data

US 2002/0047988 A1 Apr. 25, 2002

(30) Foreign Application Priority Data

Mar. 17, 2000 (JP) ........................................ 2000-076134

(51) Int. Cl.⁷ .................................................. A61B 3/14
(52) U.S. Cl. ..................................................... 351/206
(58) Field of Search .............................. 351/200, 205, 351/206; 358/515, 518, 523, 527; 345/589, 593, 600

(56) References Cited

U.S. PATENT DOCUMENTS

| 4,820,037 A | 4/1989 | Kohayakawa et al. ...... 351/211 |
| 4,848,896 A | 7/1989 | Matsumoto ................. 351/211 |
| 4,952,049 A | 8/1990 | Matsumoto ................. 351/211 |
| 5,233,372 A | 8/1993 | Matsumoto ................. 351/211 |
| 5,237,400 A | * 8/1993 | Washio et al. ............. 358/518 |
| 5,455,644 A | 10/1995 | Yazawa et al. ............. 351/206 |
| 5,847,805 A | 12/1998 | Kohayakawa et al. ...... 351/210 |
| 6,158,864 A | 12/2000 | Masuda et al. ............. 351/206 |

FOREIGN PATENT DOCUMENTS

| JP | 7-111983 | 5/1995 |
| JP | 8-38430 | 2/1996 |
| JP | 8-196508 | 8/1996 |

\* cited by examiner

Primary Examiner—George Manuel
(74) Attorney, Agent, or Firm—Fitzpatrick, Cella, Harper & Scinto

(57) ABSTRACT

There is disclosed an ophthalmic imaging apparatus, comprising an image pickup for capturing an image of an eye to be examined, a memory for storing digital data of the image captured by the image pickup, a display for displaying the image stored in the memory, a first color balancer for adjusting a color balance of the captured image before storing the image in the memory, a second color balancer for adjusting a color balance of the displayed image on the display, and a controller for controlling the first color balancer based on the adjustment of the second color balancer, so that the color balance of the captured image can exactly be calibrated in a short time.

9 Claims, 3 Drawing Sheets

OPHTHALMIC IMAGING APPARATUS

BACKGROUND OF THE INVENTION

1. Field of the Invention

The present invention relates to an ophthalmic imaging apparatus such as a fundus camera for use in an ophthalmic clinic, particularly to color balance calibration.

2. Related Background Art

A system is known in which an image pickup is used to electronically capture an eye fundus image of an eye to be examined (patient's eye). This system is exclusive for a specific purpose of eye fundus image pickup. Therefore, a color balance of the image pickup is usually prefixed at a specific value, and cannot be adjusted. The eye fundus image usually has a subtle hue mainly of red and white, and an ophthalmologist diagnoses eye illness based on the image. However, since a large number of electronic apparatuses are disposed between the image pickup and a display or in a periphery of the image pickup, the image hue sometimes changes subtly by electromagnetic influences of the apparatuses. If tone of the obtained eye fundus image changes, it is possibly difficult for the ophthalmologist to diagnose the image.

The color balance can also be adjusted by storing a digital eye fundus image once in a memory and subjecting the image using a software image processing. However, much time is required for the image processing. Additionally, signal level and digital data linearity are deteriorated by quantization noise, and image quality is possibly deteriorated.

Moreover, in order to obtain a desired tone of a final output image, the color balance of a display, printer or another output apparatus itself can also be adjusted. However, when the output apparatus itself is individually adjusted, the color balance of a display portion other than the eye fundus image, or an image from another input apparatus is deteriorated, and the entire image cannot easily be seen.

SUMMARY OF THE INVENTION

A main object of the present invention is to improve an ophthalmic imaging apparatus. One of concrete objects of the present invention is to provide an ophthalmic imaging apparatus in which a color balance of a captured image can exactly be calibrated in a short time.

To achieve the objects, according to the present invention, there is provided an ophthalmic imaging apparatus, comprising: an image pickup for capturing an image of an eye to be examined; a memory for storing digital data of the image captured by the image pickup; a display for displaying the image stored in the memory; a first color balancer for adjusting a color balance of the captured image before storing the image in the memory; a second color balancer for adjusting a color balance of the displayed image on the display; and a controller for controlling the first color balancer based on the adjustment of the second color balancer.

Further objects and forms of the present invention will be apparent in the following description of an embodiment.

DETAILED DESCRIPTION OF THE PREFERRED EMBODIMENTS

Figure 1:
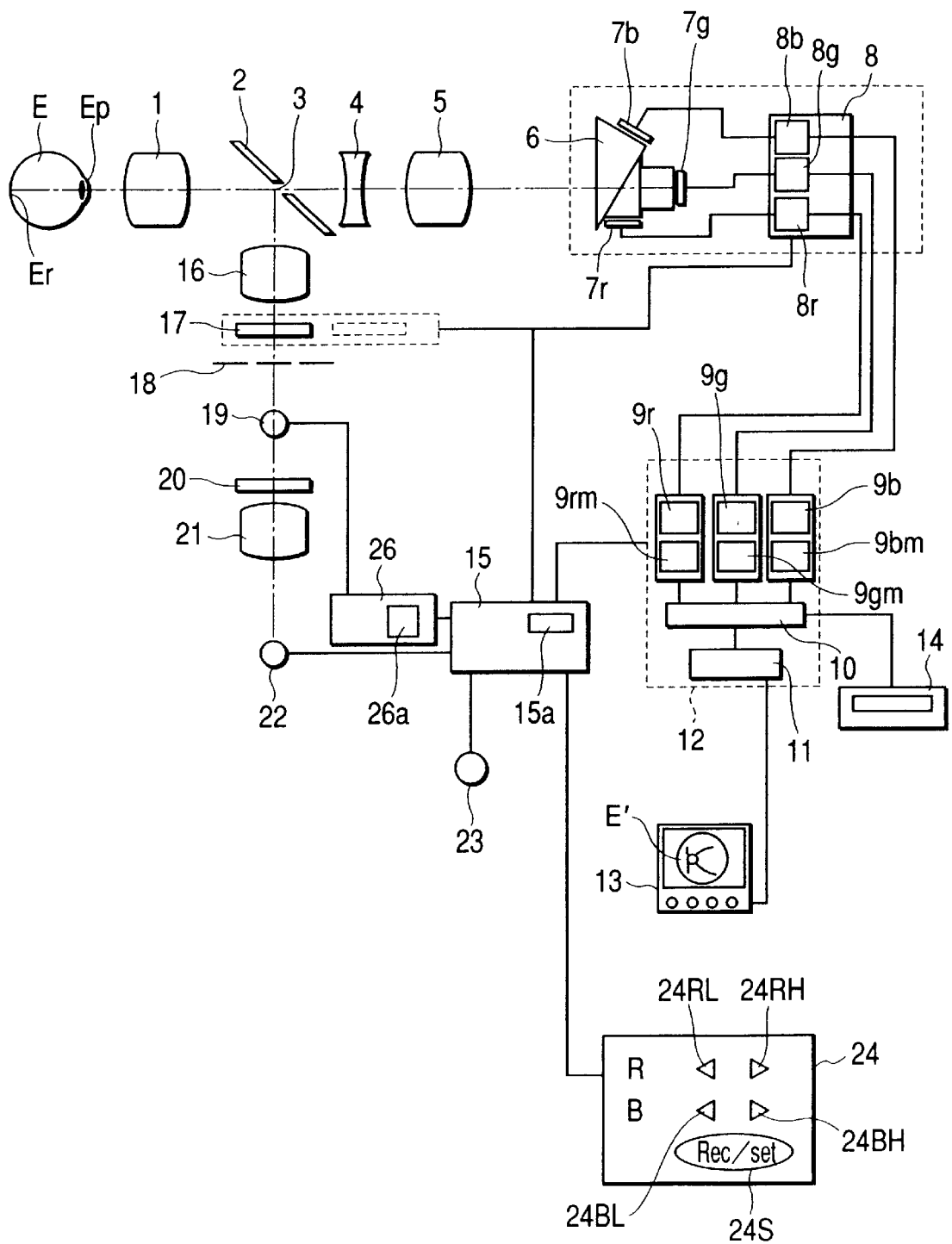
FIG. 1 is a schematic view showing an embodiment of a fundus camera.

FIG. 1 is a schematic view showing a fundus camera as an example of an ophthalmic imaging apparatus to which the present invention is applied. Additionally, the application range of the present invention is not limited to the fundus camera, and can broadly be extended to an imaging apparatus in which a subtle color balance is requested to be calibrated.

In FIG. 1, an eye fundus Er and pupil Ep of a patient's eye E are shown. An objective lens 1, and a perforated mirror 2 with a capture diaphragm 3 (aperture) formed therein are disposed opposite to the eye E, and a focus lens 4 and capture lens 5 movable on an optical axis are further disposed. An image pickup unit including a color separation prism 6 and three image pickup elements 7b, 7r, 7g is positioned behind the capture lens 5. Here, the color separation prism 6 separates color such that an infrared light and red light are guided to the image pickup element 7r, a blue light is guided to the image pickup element 7b, and a green light is guided to the image pickup element 7g. RGB signals outputted from three image pickup elements 7r, 7b, 7g of the image pickup are inputted to a first color balancer 8 (including amplifiers 8b, 8r, 8g which can individually change amplifying ratios of respective RGB colors) for adjusting the amplifying ratios of the respective colors to adjust a color balance. The respective signals individually amplified by the color balancer 8 are inputted to an imaging unit 12. The imaging unit 12 is constituted of A/D converters 9r, 9g, 9b for converting analog signals of the respective RGB colors to digital signals, image memory for storing digital image data (including image memories 9bm, 9rm, 9gm for the respective RGB colors), second color balancer 10 (data converter), and video RAM 11 for storing a displayed image. The imaging unit 12 is connected to a color display 13 such as CRT and liquid crystal display for displaying a captured image, storage device 14, and controller 15. The storage device 14 is a storage medium for holding data even if power supply from the outside is not maintained, such as MO, MD, DVD-RAM, VCR, and hard disk.

On the other hand, on the other side of the perforated mirror 2, a relay lens 16, an infrared cut filter 17, provided with a mechanism detachably attached to an optical path, for cutting the infrared light, a diaphragm 18 having an annular opening, a strobe light source 19 for emitting a flashlight, a visible cut filter 20 for cutting a visible light and transmitting the infrared light, a condenser lens 21, and an observation light source 22 (halogen lamp for emitting a stationary light including visible and infrared ranges) are arranged in order. These members including the perforated mirror 2 and objective lens 1 constitute a fundus lighting system.

The controller 15 controls the entire apparatus, and is connected to the amplifiers 8b, 8r, 8g, observation light source 22, capture switch 23, color balance calibrating operation device 24, and strobe control circuit 26. In the color balance calibrating operation device 24, push buttons 24RL, 24RH, 24BL, 24BH for individually adjusting a red and blue balance, and a determining push button 24S are arranged on a panel. Moreover, the strobe control circuit 26 controls light emission of the strobe light source 19, and controls a light emission amount in accordance with a voltage applied to a condenser 26a in the circuit.

Figure 2:
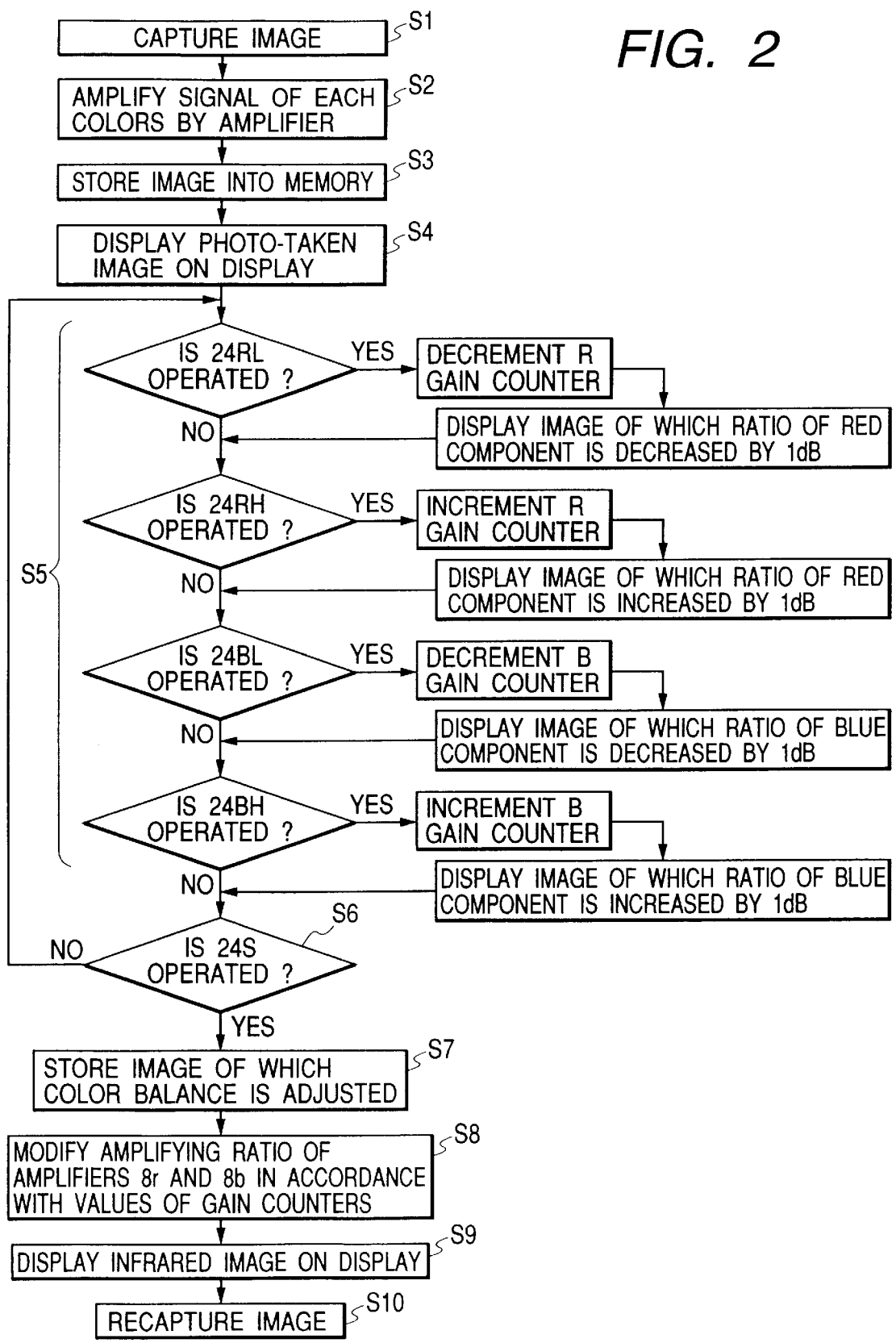
FIG. 2 is a flowchart showing an operation procedure of an apparatus during calibration of a color balance.

Operation of the apparatus constituted as described above will next be described. FIG. 2 is a flowchart showing an operation procedure of the apparatus. A person to be examined sits down in front of the fundus camera, and positions one's eye E as shown in FIG. 1. An operator who photographs the image observes an infrared dynamic image of the eye fundus Er displayed on the display 13, and positions an optical system of the fundus camera with respect to the eye E. During observation in which infrared observation is possible, the filter 17 retreats outside the optical path. The light of the observation light source 22 is focused by the condenser lens 21, and only the infrared light transmitted through the visible cut filter 20 is passed through the capture light source 19, aperture of the diaphragm 18 and lens 16 and reflected toward the left side by a peripheral mirror portion of the perforated mirror 2 to reach the eye E via the objective lens 1. Moreover, the light is transmitted through the pupil Ep to lighten the eye fundus Er. A reflected light from the eye fundus Er irradiated with the infrared light is incident upon the color separation prism 6 via the objective lens 1, capture diaphragm 3 of the perforated mirror 2, focus lens 4, and capture lens 5. The color separation prism separates and introduces the infrared light into the image pickup element 7r. An infrared image formed on the image pickup element 7r is converted to an electric signal, and the signal is amplified by the amplifier 8r and inputted to the imaging unit 12. As a result, a dynamic image is monochromatically displayed as an eye fundus image E' on the display 13. While observing the infrared eye fundus image E' displayed on the display 13, the operator positions the optical system with respect to the eye E, further moves the focus lens 4 to focus the image, and checks a capture range on the display. After checking the range, the operator photographs the image. The subsequent procedure is shown in the flowchart of FIG. 2.

When the operator presses the capture switch 23, a static image is captured in accordance with a command of the controller 15 (S1 of FIG. 2). The controller 15 detects a signal from the capture switch 23 as a trigger, inserts the filter 17 into the optical path, starts accumulating lights of the image pickup elements 7r, 7g, 7b, and controls the apparatus to send a light emitting signal to the control circuit 26. The strobe light source 19 having received the light emitting signal emits the light in accordance with an electric charge stored in the condenser 26a. Similarly as the observation light, the light of the strobe light source 19 passes through the aperture of the diaphragm 18, the infrared light is removed by the filter 17, and the remaining visible light passes through the lens 16, and is reflected toward the left side by the peripheral mirror portion of the perforated mirror 2 to lighten the eye fundus Er via the objective lens 1. The reflected light from the eye fundus Er irradiated with the visible light is incident upon the color separation prism 6 via the objective lens 1, capture diaphragm 3, focus lens 4, and capture lens 5. The color separation prism 6 separates the visible light into respective color components of red, green, blue, and the respective RGB color components are formed into images on the image pickup elements 7r, 7g, 7b. The amplifiers 8r, 8g, 8b amplify the signals of the respective colors with set amplifying ratios (S2 of FIG. 2). The color balance of the taken image is determined by the amplifying ratio of each amplifier.

Subsequently, image data digitized by the imaging unit 12 are stored in the image memories 9rm, 9gm, 9bm for the respective colors (S3 of FIG. 2). In an initial state, the second color balancer 10 transfers the data stored in the memories 9rm, 9gm, 9bm as they are to the video RAM 11 without changing the color balance. The display 13 color-displays content of the video RAM 11 as the eye fundus image E' (S4 of FIG. 2).

The operator sees and judges the displayed image on the display 13. If image tone is satisfactory, the capturing of the image is completed, and image data is stored in the storage device 14. On the other hand, if the operator judges that it is necessary to modify the color balance, the operator operates the operation device 24 to adjust the tone of red and blue components. Concretely, the push button 24RH increases the red component, the push button 24RL decreases the red component, and these buttons constitute a red component adjuster. Moreover, the push button 24BH increases the blue component, the push button 24BL decreases the blue component, and these buttons constitute a blue component adjuster. Additionally, the adjuster is not limited to the push button, and an analog adjuster may also be used. For example, when the image is too reddish, and the red component is to be decreased, the operator presses the push button 24RL to decrease the red component. The controller 15 detects this, and decrements an R gain counter set in a memory 15a of the controller 15 by the number of times by which the push button 24RL is pressed (or time when the button is pressed). The color balancer 10 converts data to a digital level based on the R gain counter so as to reduce the red component data (data of the memory 9rm), and transfers the level to the video RAM 11. As a result, the tone of the displayed image of the display 13 changes (the red component decreases). Moreover, for example, when the blue color is strengthened, the operator presses the push button 24BH. In this case, a B gain counter in the memory 15a is incremented, the color balancer 10 converts data to the digital level so as to increase the blue component data (memory 9bm), and therefore the blue component of the displayed image on the display 13 is emphasized. As described above, by a superior user interface in which the operation of the operation device 24 is reflected and the tone of the displayed image changes in real time, the operator can immediately judge whether or not the desired tone is obtained.

The operator having confirmed that the displayed image bears the desired tone presses the push button 24S to determine setting. The controller 15 detects this (S6 of FIG. 2), transmits a command to the imaging unit 12, and stores data of the eye fundus image E' having the same color balance as that of the image displayed on the display 13 into the storage device 14 (S7 of FIG. 2). Additionally, the amplifying ratios of the amplifiers 8r, 8b for amplifying image pickup signals are set in accordance with the value held by the gain counter 15a of the controller. For example, when the value of the R gain counter is −3, the set gain of the amplifier 8r is decreased (for example, to −3 dB). When the value of the B gain counter is +5, the set gain of the amplifier 8b is increased (for example, to +5 dB) (S8 of FIG. 2). Thereafter, the gain counter is reset. Here, among the three RGB components, red and blue are adjusted based on green for the following reason. That is, the image captured by the fundus camera has a tone containing the red component (mainly of blood vessel) most. Such characteristics are utilized. At least the red having a largest influence is adjusted, and adjustment of green is omitted. As a modification example, the adjuster is disposed only for the red component most influencing the entire tone, and adjustment of blue and green may be omitted. Alternatively, a green adjuster is also added to the operation device 24, and the gain of the amplifier 8g may also be adjusted together with other colors.

The gain setting of the first color balancer, that is, the calibration of the color balance of the captured image is completed in this manner. Thereafter, the apparatus is brought to an image recapturing mode, and the display 13 displays the dynamic infrared image as described above (S9 of FIG. 2). The operator sees this display, checks a positioned state, and presses the capture switch 23 to recapture the image (S10 of FIG. 2). Here, the signals of the image pickup elements 7r, 7g, 7b are individually amplified with the individual amplifying ratios of the amplifiers 8r, 8g, 8b, and the captured image obtains the tone desired by the operator from the first time.

Figure 3:
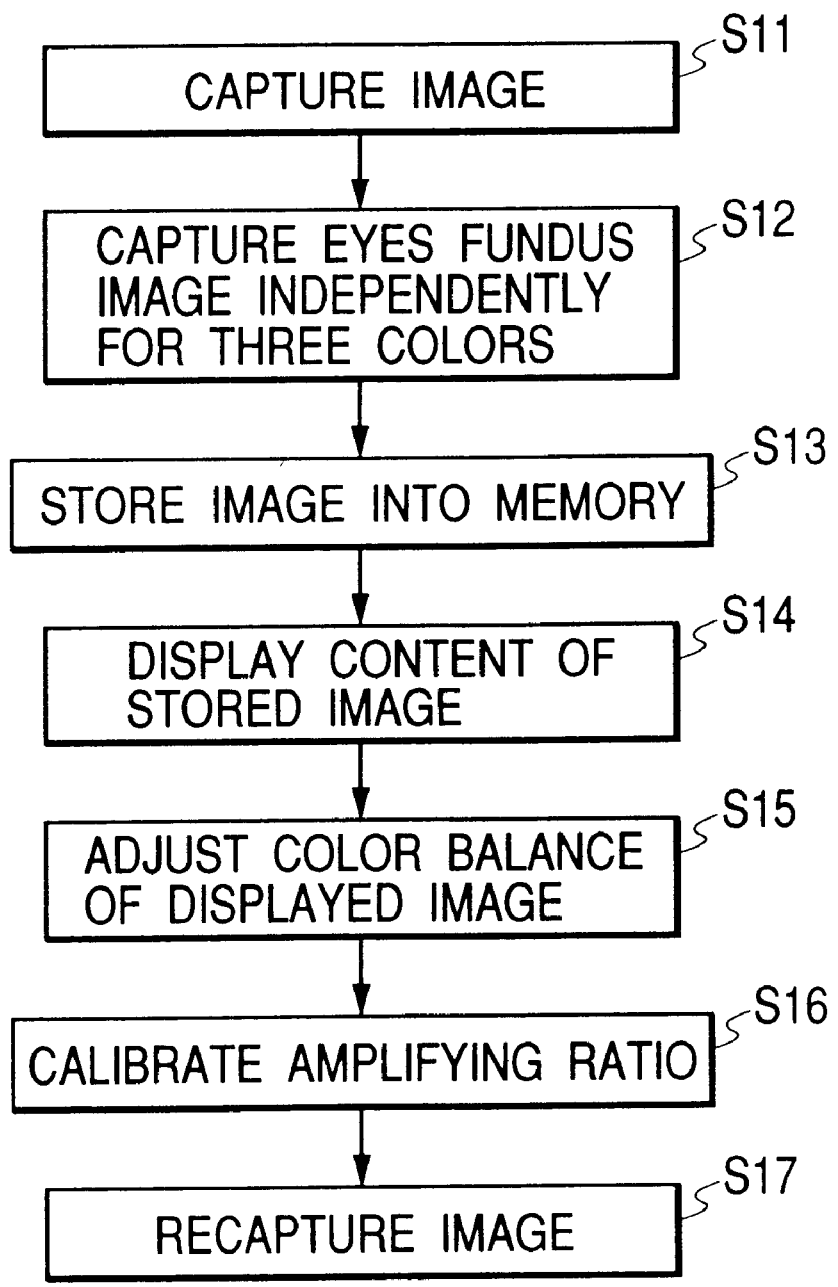
FIG. 3 is a flowchart showing summary of a color balance calibration procedure.

FIG. 3 is a flowchart showing summary of the aforementioned calibration procedure. The procedure includes steps of capturing the image (S11), capturing the eye fundus images independently for three RGB colors (S12), storing the image into the memory (S13), displaying the memory content on the display (S14), subsequently adjusting the color balance of the displayed image by the second color balancer (S15), and individually calibrating the amplifying ratios of the amplifiers by the first color balancer based on the setting (S16). After the calibration, the image is recaptured (actually captured). During the recapturing of the image, a broad dynamic range of the A/D converter can effectively be utilized, information amount of gradation is increased, and image quality is further enhanced. Moreover, preliminary image capture may be performed only once for calibration. Therefore, a burden on the person to be examined is small.

Additionally, in the aforementioned example, when the amplifiers 8r, 8g, 8b of the first color balancer individually adjust the amplifying ratios of the respective RGB signals, the color balance is adjusted. As the modification example, when standard voltages of the A/D converters 9r, 9g, 9b are individually changed, the color balance can be adjusted. For example, a case in which an analog standard voltage 0.7 V corresponds to a digital value 255, and 0 V corresponds to a digital value 0 during A/D conversion is compared with a case in which the standard voltage is changed to 0.6 V and A/D conversion is performed. Then, 0.7 V is substantially amplified by about 17% (0.7/0.6=1.16666) with respect to 0.6 V. That is, instead of the amplifier amplifying ratio, the standard voltages of the A/D converters 9r, 9g, 9b are set to be variable and used as the first color balancer. Then, the color balance of the captured image can be calibrated.

What is claimed is:

1. An ophthalmic apparatus, comprising:

an image pickup which captures an image of an eye to be examined;

a memory which stores digital image data captured by the image pickup;

a display which displays the image stored in the memory;

a first color balancer which adjusts a color balance of the captured image before storing in the memory;

a second color balancer which adjusts a color balance of the displayed image on the display; and a controller which controls the first color balancer based on the adjustment of the second color balancer.

2. An apparatus according to claim 1, further comprising an operation device, electrically connected to said controller, allowing an operator to adjust the color balance of the displayed image with said second color balancer.

3. An apparatus according to claim 2, wherein said image pickup comprises three pickup elements to obtain RGB signals.

4. An apparatus according to claim 3, wherein said operation device includes an adjuster for adjusting a red color component.

5. An apparatus according to claim 4, wherein said first color balancer comprises adjustable amplifiers each corresponding to one of the RGB signals respectively.

6. An apparatus according to claim 4, wherein said first color balancer comprises adjustable A/D converters each corresponding to one of the RGB signals respectively.

7. An apparatus according to claim 3, wherein said operation device includes a first adjuster for adjusting a red color component and a second adjuster for adjusting a blue color component.

8. An apparatus according to claim 3, wherein said first color balancer comprises adjustable amplifiers each corresponding to one of the RGB signals respectively.

9. An apparatus according to claim 3, wherein said first color balancer comprises adjustable A/D converters each corresponding to one of the RGB signals respectively.

\* \* \* \* \*

UNITED STATES PATENT AND TRADEMARK OFFICE
CERTIFICATE OF CORRECTION

PATENT NO. : 6,488,377 B2
DATED : December 3, 2002
INVENTOR(S) : Kazuhiro Matsumoto It is certified that error appears in the above-identified patent and that said Letters Patent is hereby corrected as shown below:

Column 4,
Line 40, "setting" should read -- the setting --.
Line 55, "containing the" should read -- containing mostly the --.
Line 56, "vessel) most." should read -- vessel). --.

Signed and Sealed this

Twenty-second Day of July, 2003

JAMES E. ROGAN
Director of the United States Patent and Trademark Office